United States Patent
Cunningham

(10) Patent No.: US 9,452,195 B2
(45) Date of Patent: Sep. 27, 2016

(54) USE OF CHEC PEPTIDES TO TREAT NEUROLOGICAL AND CARDIOVASCULAR DISEASES AND DISORDERS

(75) Inventor: Timothy J. Cunningham, Fort Washington, PA (US)

(73) Assignee: Drexel University, Philadelphia, PA (US)

( * ) Notice: Subject to any disclaimer, the term of this patent is extended or adjusted under 35 U.S.C. 154(b) by 441 days.

(21) Appl. No.: 13/640,192

(22) PCT Filed: Mar. 28, 2011

(86) PCT No.: PCT/US2011/030192
§ 371 (c)(1),
(2), (4) Date: Feb. 19, 2013

(87) PCT Pub. No.: WO2011/126804
PCT Pub. Date: Oct. 13, 2011

(65) Prior Publication Data
US 2013/0143792 A1  Jun. 6, 2013

Related U.S. Application Data

(60) Provisional application No. 61/322,540, filed on Apr. 9, 2010.

(51) Int. Cl.
*A61K 38/08* (2006.01)

(52) U.S. Cl.
CPC ..................... *A61K 38/08* (2013.01)

(58) Field of Classification Search
None
See application file for complete search history.

(56) References Cited

U.S. PATENT DOCUMENTS

| 6,262,024 B1 | 7/2001 | Cunningham et al. | |
| 7,528,112 B2 | 5/2009 | Cunningham et al. | |
| 2008/0249027 A1 * | 10/2008 | Cunningham et al. | ......... 514/16 |
| 2009/0181879 A1 | 7/2009 | Cunningham et al. | |
| 2009/0286746 A1 | 11/2009 | Cunningham et al. | |

OTHER PUBLICATIONS

Pilitsis et al. (Differential effects of phospholipase inhibitors on free fatty acid efflux in rat cerebral cortex during ischemia-reperfusion injury, Brain Research 951 (2002) 96-106).*
Farooqui et al. (Inhibitors of Brain Phospholipase A2 Activity: Their neuropharmacological Effects and Therapeutic Importance for the Treatment of Neurologic Disorders: Pharmacological Reviews: 2006, 58: 591-620).*
Adibhatla et al., "Altered lipid metabolism in brain injury and disorders." 2008 Subcell Biochem 49:241-268.
Cunningham et al. "Caireticulin binding and other biological activities of survival peptide Y-P30 including effects of systemic treatment of rats.", 2000, Exp. Neurol. 163:457-468.
Cunningham, et al., "Identification of a survival-promoting peptide in medium conditioned by oxidatively stressed cell lines of nervous system origin." 1998, J. Neurosci. 18:7047-7060.
Cunningham, et al., "Identification of the human cDNA for new survival/evasion peptide (DSEP): studies in vitro and in vivo of overexpression by neural cells." 2002, Exp. Neurol. 177:32-39.
Hanasaki and Arita, "Phospholipase A2 receptor: a regulator of biological functions of secretory phospholipase A2." 2002, Prostaglandins Other Lipid Mediat. 68-69:71-82.
Thwin et al., "Secretory phospholipase A2 activity in the normal and kainate injected rat brain, and inhibition by a peptide derived from python serum." 2003, Exp. Brain Res. 150:427-433.
Wang, et al., "Neuroprotective effects of a nanocrystal formulation for sPLA2 Inhibitor PX-18 in cerebral ischemia/reperfusion in gerbils." 2009, Brain Res 1285:188-195.

* cited by examiner

*Primary Examiner* — James H Alstrum Acevedo
*Assistant Examiner* — Tara Martinez
(74) *Attorney, Agent, or Firm* — Saul Ewing LLP; Kathryn Doyle

(57) ABSTRACT

The present invention describes compositions and methods for treating and preventing non-degenerative neurological diseases and disorders associated with elevated sPLA2 activity as well as cardiovascular diseases using a CHEC peptide to inhibit sPLA2 activity.

8 Claims, 3 Drawing Sheets

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Chemically synthesized

<400> SEQUENCE: 1

Cys His Glu Ala Ser Ala Ala Gln Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Chemically synthesized

<400> SEQUENCE: 2

Cys Ala His Ala Gln Ala Glu Ser Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Chemically synthesized

<400> SEQUENCE: 3

Cys His Glu Ala Ser Gln Cys
1               5

<210> SEQ ID NO 4
<211> LENGTH: 27
<212> TYPE: DNA
<213> ORGANISM: Artificial Sequence
<220> FEATURE:
<223> OTHER INFORMATION: Chemically synthesized
```

```
<400> SEQUENCE: 4
tgccatgaag catcagcagc tcaatgc                                27

<210> SEQ ID NO 5
<211> LENGTH: 27
<212> TYPE: DNA
<213> ORGANISM: Artificial Sequence
<220> FEATURE:
<223> OTHER INFORMATION: Chemically synthesized

<400> SEQUENCE: 5
tgccatgaag catcagcagc tcaatgt                                27

<210> SEQ ID NO 6
<211> LENGTH: 21
<212> TYPE: DNA
<213> ORGANISM: Artificial Sequence
<220> FEATURE:
<223> OTHER INFORMATION: Chemically synthesized

<400> SEQUENCE: 6
tgccatgaag catcacaatg c                                      21

<210> SEQ ID NO 7
<211> LENGTH: 21
<212> TYPE: DNA
<213> ORGANISM: Artificial Sequence
<220> FEATURE:
<223> OTHER INFORMATION: Chemically synthesized

<400> SEQUENCE: 7
tgccatgaag catcacaatg t                                      21
```

USE OF CHEC PEPTIDES TO TREAT NEUROLOGICAL AND CARDIOVASCULAR DISEASES AND DISORDERS

CROSS-REFERENCE TO RELATED APPLICATION

This application is the U.S. national phase application filed under 35 U.S.C. §371 claiming benefit to International Patent Application No. PCT/US2011/030192, filed on Mar. 28, 2011, which is entitled to priority under 35 U.S.C. §119(e) to U.S. Provisional Patent Application No. 61/322,540 filed on Apr. 9, 2010, each of which application is hereby incorporated herein by reference in its entirety.

BACKGROUND OF THE INVENTION

Phospholipase A2s (PLA2s) are an expanding super family of esterases that cleave the acyl ester bond at the sn-2 position of membrane phospholipids to produce a free fatty acid and lysophospholipid (Farooqui et al., 2000, Neuroscientist 6:169-180). Because a large proportion of cellular arachidonic acid is found esterified at the sn-2 position of membrane phospholipids, arachidonic acid and lysophospholipid are the major products of the PLA2-catalyzed reaction. Under normal conditions, some arachidonic acid is converted to inflammatory mediators, prostaglandins, leukotrienes, and thromboxanes, whereas a majority of arachidonic acid is reincorporated into brain phospholipids (Rapoport, 1999, Neurochem. Res. 24:1403-1415; Leslie, 2004, Biochem. Cell. Biol. 82:1-17). Arachidonic acid not only acts via conversion to inflammatory metabolites, but can also directly modulate neuronal function by various mechanisms, such as altering membrane fluidity and polarization state, activating protein kinase C, and regulating gene transcription (Katsuki and Okuda, 1995, Prog. Neurobiol. 46:607-636; Farooqui et al., 1997 Arachidonic acid, neurotrauma, and neurodegenerative disease, in Handbook of Essential Fatty Acid Biology (Yehuda and Mostofsky, eds.) pp 277-295, Humana Press, Totowa, N.J.). Another product of PLA2 catalyzed reactions, 1-alkyl-2-lysophospholipid, is the immediate precursor of platelet-activating factor (PAF), another potent inflammatory mediator (Farooqui and Horrocks, 2004, Plasmalogens, platelet activating factor, and other lipids, in Bioactive Lipids (Nicolaou and Kokotos, eds.) pp 107-134, Oily Press, Bridgwater, U.K.).

Increased PLA2 activity and excessive production of proinflammatory mediators, eicosanoids, and platelet activating factor, may potentially lead to disease states and neuronal injury. PLA2-generated mediators play a central role not only in acute inflammatory responses in brain but also in oxidative stress associated with progressive degenerative neurological disorders such as Alzheimer's disease (AD), Parkinson's disease (PD), and multiple sclerosis (MS) (Kalyvas and David, 2004, Neuron 41:323-335; Phillis and O'Regan, 2004, Brain Res. Rev. 44:13-47; Sun et al., 2004, J. Lipid Res. 45:205-213). PLA2 contributes to the pathogenesis of the above disorders by attacking neural membrane phospholipids and releasing proinflammatory lipid mediators such as prostaglandins, leukotrienes, and thromboxanes, and PAF, and also by generating 4-hydroxynonenal (4-HNE).

Secretory phospholipase A2 (sPLA2) is synthesized intracellularly, then secreted from the cell where it acts extracellularly. PLA2 binds to two types of cell surface receptors, namely the N type in neurons, and the M type in skeletal muscles, (Hanasaki and Arita, 2002, prostaglandins Other Lipid Mediat. 68-69:71-82). Brain sPLA2 is present in all regions of mammalian brain with the highest activities of sPLA2 are found in medulla oblongata, pons, and hippocampus, moderate activities in the hypothalamus, thalamus, and cerebral cortex, and low activities in the cerebellum and olfactory bulb (Thwin et al., 2003, Exp. Brain Res, 150:427-433).

Glutamate and its analogs stimulate sPLA2 activity in a dose- and time-dependent manner (Kim et al., 1995, Biochem. J. 310:83-90; Xu et al., 2003, Free Radical Biol. Med. 34:1531-1543). The neurotoxicity of glutamate is synergistically increased with the addition of sPLA2 to cortical cultures, suggesting glutamatergic synaptic activity may be modulated by sPLA2 and its receptors on the neuronal surface (DeCoster et al., 2002, J. Neurosci. Res. 67:634-645; Kolko et al., 2002, NeuroReport 13:1963-1966). In PC12 cells, sPLA2 induces neurite outgrowth. Mutants with reduced sPLA2 activity exhibit a comparable reduction in neurite-inducing activity (Nakashima et al., 2003, Biochem. J. 376:655-666), indicating that sPLA2 performs a neurotrophin-like role in the central nervous system.

Neurons are more susceptible to free radical-mediated neuroinflammation and oxidative stress than glial cells (Adibhatla et al., 2003, J. Neurosci. Res. 73:308-315; Ajmone-Cat et al., 2003, J. Neurochem. 87:1193-1203). In fact, activated glial cells, including astroglia and microglia, sustain inflammatory processes initiated by arachidonic acid-generated metabolites. This suggests that signals modulating the induction, expression, and stimulation of PLA2 isoforms may play an important role in neurodegenerative diseases associated with Neuroinflammation and oxidative stress (Farooqui and Horrocks, 1994, Int. Rev. Neurobio, 36:267-323; Farooqui et al., 2003, Stimulation of lipases and phospholipases in Alzheimer disease, in Nutrition and Biochemistry of Phospholipids (Szuhaj and van Nieuwenhuyzen, eds.) pp 14-29 AOCS Press, Champaign, Ill.; Farooqui and Horrocks, 2004, Plasmalogens, platelet activating factor, and other lipids, in Bioactive Lipids (Nicolaou and Kokotos, eds.) pp 107-134, Oily Press, Bridgwater, U.K.). For the successful treatment of inflammatory and oxidative stress in neurological disorders, timely delivery of a well-tolerated, chronically active, and specific inhibitor of PLA2 that can bypass or cross the blood-brain barrier without harm is required. Some nonspecific PLA2 inhibitors have been used for the treatment of neurological disorders such as ischemia, spinal cord injury, and AD (Sano et al., 1997, New Eng. J. med. 336:1216-1222), but no compound with real clinical potential has emerged.

The neuron survival-promoting peptide Y-P30 was originally identified in the secretions of neural cells (neuroblastoma and retinoblastoma) subjected to oxidative stress (Cunningham, et al. 1998, J. Neurosci. 18:7047-7060). Partially purified fractions of conditioned culture medium were screened in vitro until the active Y-P30 peptide was identified—the synthetic version of this peptide was then tested in vitro and in vivo and found to support neural cells which were degenerating for a variety of reasons, including oxidative stress and central nervous system trauma (Cunningham, et al. 1998, J. Neurosci. 18:7047-7060; Cunningham et al., 2000, Exp. Neurol. 163:457-468). This peptide was later confirmed to be part of an endogenous human polypeptide (~12 kiloDaltons) named DSEP after identification of the human cDNA encoding DSEP and the locus of the DSEP gene in human chromosomal region 12q (Cunningham, et al. 2002, Exp. Neurol. 177:32-39). In that study, it was found that overexpression of the full length polypeptide in neural cells made them resistant to several forms of oxidative stress including that resulting from immune cell attack. CHEC-9 and CHEC-7 are anti-inflammatory and neuron survival-promoting peptides that inhibit enzymes that initiate a cascade of changes during the early stages of inflammation.

The stimulation of sPLA2 and subsequent biochemical cascade are important events associated with acute neural trauma as well as chronic neurological degenerative diseases (Farooqui et al., 2006, Pharmacological Rev. 58:591-620). Similarly, atherosclerosis has been proposed as both a disorder of inflammation and lipid metabolism (Jaross et al., 1999, Atherosclerosis 144 (Supplement 1):119-120). The sPLA2s are a subclass of phospholipase A2 enzymes that cleave the A2 fatty acid ester of phospholipids (Burke et al, 2009, J. Lipid Res. 50:S237-242). Several sPLA2s have been identified and the contribution of specific enzyme isoforms (principally groups II, V and X) and play a role in the formation of atherosclerotic lesions (Rosenson, 2009, Cardiovascular Drugs and Therapy 23:93-101). sPLA2 inhibitors are attractive therapeutic targets. However, existing and available sPLA2 inhibitors lack sufficient specificity, affecting not just other PLA2 isoforms, but other enzymes such as cyclooxygenase and acyltransferase (Cummings et al., 2000, J. Pharmacal. Exp. Ther. 294:793-799; Fuentes et al., 2003, J. Biol. Chem. 278:44683-44690).

There is a long standing need in the art for specific and potent sPLA2 inhibitors that are well-tolerated clinically for use in methods of treating a variety of non-degenerative neurological diseases or disorders and cardiovascular diseases. The present invention fills this need.

SUMMARY OF THE INVENTION

The invention includes a method of treating a mammal afflicted with a non-degenerative neurological disease or disorder associated with elevated levels of secreted phospholipase A2 (sPLA2) activity. The method comprises administering a pharmaceutical composition comprising an effective amount of a sPLA2 inhibitor to the mammal, thereby treating the non-degenerative neurological disease or disorder in the mammal. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide. In yet another embodiment, the non-degenerative neurological disease or disorder is selected from the group consisting of epilepsy, ischemic injury, schizophrenia, and a mood disorder.

The invention also includes a method of treating a mammal at risk of developing a non-degenerative neurological disease or disorder associated with an elevated level of secreted phospholipase A2 (sPLA2) activity. The method comprises administering a pharmaceutical composition comprising an effective amount of a sPLA2 inhibitor to the mammal, thereby treating the mammal at risk of developing the non-degenerative neurological disease or disorder. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide. In yet another embodiment, the non-degenerative neurological disease or disorder is selected from the group consisting of epilepsy, ischemic injury, schizophrenia, and a mood disorder.

The invention further includes a method of treating a mammal afflicted with epilepsy wherein sPLA2 activity is elevated. The method comprises administering a pharmaceutical composition comprising an effective amount of a sPLA2 inhibitor to the mammal, wherein when an effective amount of the sPLA2 inhibitor contacts a neuron in the central nervous system, the sPLA2 inhibitor specifically inhibits the sPLA2 activity in the neuron, wherein the sPLA2 inhibitor treats the epilepsy in the mammal. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide.

The invention further includes a method of treating a mammal at risk of having a seizure wherein sPLA2 activity is elevated. The method comprises administering a pharmaceutical composition comprising an effective amount of a sPLA2 inhibitor to the mammal, wherein when an effective amount of the sPLA2 inhibitor contacts a neuron in the central nervous system, the sPLA2 inhibitor specifically inhibits the sPLA2 activity in the neuron, wherein the sPLA2 inhibitor treats the mammal at risk of having the seizure. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide.

The invention further includes a method of treating a mammal afflicted with a non-degenerative neurological disease or disorder associated with an elevated level of secreted phospholipase A2 (sPLA2) activity. The method comprises administering a pharmaceutical composition comprising an effective amount of a sPLA2 inhibitor to the mammal, wherein when the sPLA2 inhibitor contacts a neuron in the central nervous system, the sPLA2 inhibitor specifically inhibits the sPLA2 activity in the neuron, thereby treating the non-degenerative neurological disease or disorder in the mammal. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide. In yet another embodiment, the non-degenerative neurological disease or disorder is selected from the group consisting of epilepsy, ischemic injury, schizophrenia, and a mood disorder.

The invention further includes a method of treating a mammal at risk of developing a non-degenerative neurological disease or disorder associated with an elevated level of secreted phospholipase A2 (sPLA2) activity. The method comprises administering a pharmaceutical composition comprising an effective amount of a sPLA2 inhibitor to the mammal, wherein when the sPLA2 inhibitor contacts a neuron in the central nervous system, the sPLA2 inhibitor specifically inhibits the sPLA2 activity in the neuron, thereby treating the mammal at risk of developing the non-degenerative neurological disease or disorder. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide. In yet another embodiment, the non-degenerative neurological disease or disorder is selected from the group consisting of epilepsy, ischemic injury, schizophrenia, and a mood disorder.

The invention further includes a method of treating a mammal afflicted with epilepsy associated with an elevated level of secreted phospholipase A2 (sPLA2) activity. The method comprises administering a pharmaceutical composition comprising an effective amount of a sPLA2 inhibitor to the mammal, wherein when the sPLA2 inhibitor contacts a neuron in the central nervous system, the sPLA2 inhibitor specifically inhibits the sPLA2 activity in the neuron, thereby treating the epilepsy in the mammal. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide.

The invention further includes a method of treating a mammal at risk of developing epilepsy associated with an elevated level of secreted phospholipase A2 (sPLA2) activity. The method comprises administering a pharmaceutical composition comprising an effective amount of a sPLA2 inhibitor to the mammal, wherein when the sPLA2 inhibitor contacts a neuron in the central nervous system, the sPLA2 inhibitor specifically inhibits the sPLA2 activity in the neuron, thereby treating the mammal at risk of developing the epilepsy. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide.

In invention further includes a method of treating a mammal afflicted with a cardiovascular disease or disorder. The method comprises administering a pharmaceutical composition comprising an effective amount of a sPLA2 inhibitor to the mammal, thereby treating the cardiovascular disease or disorder in the mammal. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide. In yet another embodiment, the cardiovascular disease or disorder is selected from the group consisting of atherosclerosis, angina, cerebrovascular accident (stroke), cerebrovascular disease, transient ischemic incidents, congestive heart failure, coronary artery disease, myocardial ischemia, myocardial infarction, and peripheral vascular disease.

The invention further includes a method of treating a mammal at risk of developing a cardiovascular disease or disorder. The method comprises administering a pharmaceutical composition comprising an effective amount of a sPLA2 inhibitor to the mammal, thereby treating the mammal at risk of developing the cardiovascular disease. Preferably, the mammal is a human.

In one embodiment, the sPLA2 inhibitor is selected from the group consisting of a CHEC-9 peptide, a CHEC-7 peptide, a derivative of a CHEC-9 peptide, a derivative of a CHEC-7 peptide, and any combination thereof. In another embodiment, the sPLA2 inhibitor is selected from the group consisting of a nucleic acid encoding CHEC-9, a nucleic acid encoding CHEC-7, a nucleic acid encoding a derivative of a CHEC-9 peptide, and a nucleic acid encoding a derivative of a CHEC-7 peptide. In yet another embodiment, the cardiovascular disease or disorder is selected from the group consisting of atherosclerosis, angina, cerebrovascular accident (stroke), cerebrovascular disease, transient ischemic incidents, congestive heart failure, coronary artery disease, myocardial ischemia, myocardial infarction, and peripheral vascular disease.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
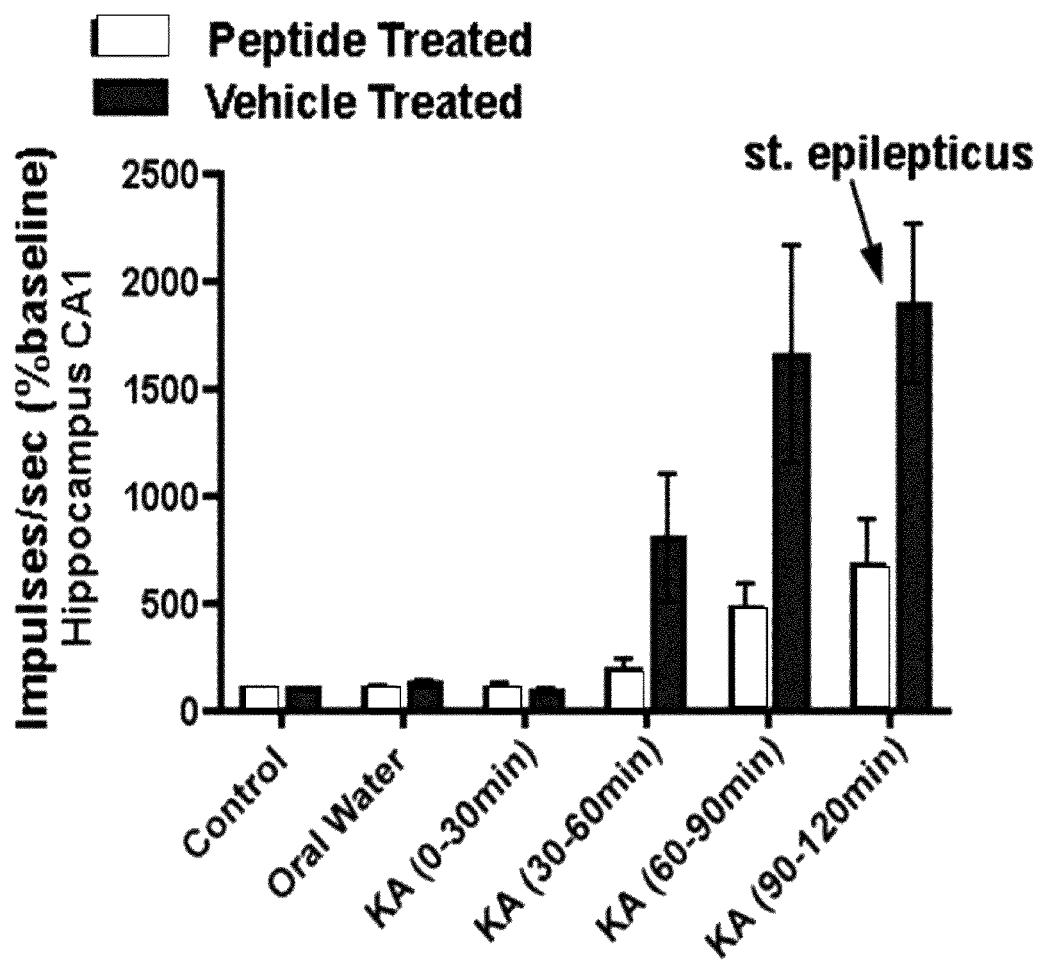
FIG. 1, is a graph depicting multiunit activity recorded from the CA1 cell field of the hippocampus of awake, freely moving kainic acid-treated rats that have been treated either with CHEC-9 or vehicle. Multiunit activity is presented as impulses recorded per second and provided as a percentage of baseline activity measured prior to seizure induction.

Previously, elevated sPLA2 activity was thought to be associated only with neurological diseases and disorders characterized by progressive neuronal death, apoptosis and degeneration. The present invention is based on the discovery that some non-degenerative neurological diseases and disorders are associated with elevated sPLA2 activity that is detectable in a body sample. As demonstrated for the first time herein, elevated sPLA2 is a therapeutic target for treating and preventing these non-degenerative neurological diseases and disorders. The present invention identifies for the first time epilepsy, ischemic injury, schizophrenia, and mood disorders as non-degenerative neurological diseases and disorders associated with elevated sPLA2 activity. The present invention should not be deemed to be limited to those non-degenerative diseases and disorders recited herein, but rather is intended to encompass all non-degenerative neurological diseases and disorders associated with elevated sPLA2 activity, both known and unknown.

In addition, the present invention is based on the discovery that inhibiting sPLA2 activity can be used to treat and prevent cardiovascular diseases and disorders, including atherosclerosis, angina, cerebrovascular accident (stroke), cerebrovascular disease, transient ischemic incidents, congestive heart failure, coronary artery disease, myocardial ischemic, myocardial infarction, and peripheral vascular disease.

CHEC-9 (SEQ ID NO. 1), a CHEC-9 peptide variant (SEQ ID NO. 2), CHEC-7 (SEQ ID NO. 3), as well as variants thereof, are collectively referred to herein as CHEC peptides. Each CHEC peptide is a potent sPLA2 inhibitor. The present invention therefore provides compositions and methods to treat a mammal afflicted with, or at risk of developing, a non-degenerative neurological disease or disorder associated with elevated sPLA2 activity, or a cardiovascular disease or disorder wherein the method comprises administering to the mammal a CHEC peptide or an isolated nucleic acid encoding a CHEC peptide.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

The practice of the present invention employs, unless otherwise indicated, conventional techniques of chemistry, molecular biology, microbiology, recombinant DNA, genetics, and immunology. See, e.g., Sambrook et al., 2001, Molecular Cloning: A Laboratory Manual, Cold Spring Harbor Laboratory Press, Cold Spring Harbor, N.Y.; Ausubel et al. 2002, Current Protocols in Molecular Biology, John Wiley & Sons, NY; Glover, 1985; Anand, 1992; Guthrie and Fink, 1991. A general discussion of techniques and materials for human gene mapping, including mapping of human chromosome 1, is provided, e.g., in White and Lalouel, 1988.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

By the term "applicator" as the term is used herein, is meant any device including, but not limited to, a hypodermic syringe, a pipette, and the like, for administering a CHAC peptide of the invention to a mammal.

The phrase "body sample" as used herein, is intended any sample comprising a cell, a tissue, or a bodily fluid in which expression of sPLA2 or sPLA2 esterase activity can be detected. Samples that are liquid in nature are referred to herein as "bodily fluids." Body samples may be obtained from a patient by a variety of techniques including, for example, by scraping or swabbing an area or by using a needle to aspirate bodily fluids. Methods for collecting various body samples are well known in the art.

The phrase "at-risk" as used herein refers to a subject with a greater than average likelihood of developing a neurological disease or disorder syndrome associated with elevated activity of sPLA2.

A "disease" is a state of health of subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In preferred embodiments, the subject is an animal. In more preferred embodiments, the subject is a mammal. In most preferred embodiments, the subject is a human.

A "mood disorder" as used herein encompasses a group of diagnoses provided in the Diagnostic and Statistical Manual of mental Disorders (DSM IV TR) classification system where a disturbance in a subject's mood is the principal presenting feature. Two groups of mood disorders are broadly recognized as depressive disorders and bipolar disorders. Depressive disorders include major depressive disorder (MDD), commonly called clinical depression or major depression, atypical depression, melancholic depression, psychotic major depression, catatonic depression, postpartum depression, seasonal afective disorder, dysthymia, depressive disorder not otherwise specified, such as recurrant brief depression and minor depressive disorder. Bipolar disorders (BD), formerly known as "manic depression" and described by intermittent periods of manic and depressed episodes, include bipolar I, bipolar II, cyclothymia, and bipolar disorder not otherwise specified. Other mood disorders include substance-induced mood disorders, such as alcohol induced mood disorders and benzodiazepine induced mood disorders.

The term "cardiovascular disease," as used herein, refers to a class of diseases that involve the heart and blood vessels (arteries and veins). Cardiovascular disease includes atherosclerosis, angina, cerebrovascular accident (stroke), cerebrovascular disease, transient ischemic incidents, congestive heart failure, coronary artery disease, myocardial ischemia, myocardial infarction, and peripheral vascular disease.

The term "atherosclerosis" as used herein refers to the condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries The term "coronary artery disease" (or CAD), as used herein, refers to the end result of the accumulation of atheromatous plaques within the walls of the coronary arteries that supply the myocardium (the muscle of the heart) with oxygen and nutrients. As the degree of coronary artery disease progresses, there may be near-complete obstruction of the lumen of the coronary artery, severely restricting the flow of oxygen-carrying blood to the myocardium. Individuals with this degree of coronary artery disease typically have suffered from one or more myocardial infarctions (heart attacks), and may have signs and symptoms of chronic coronary ischemia, including symptoms of angina at rest and flash pulmonary edema.

The term "myocardial infarction" (MI) or "acute myocardial infarction" (AMI), as used herein refer to the interruption of blood supply to part of the heart, causing some heart cells to die. This is most commonly due to occlusion (blockage) of a coronary artery following the rupture of a vulnerable atherosclerotic plaque, which is an unstable collection of lipids (fatty acids) and white blood cells (especially macrophages) in the wall of an artery. The resulting ischemia (restriction in blood supply) and oxygen shortage, if left untreated for a sufficient period of time, can cause damage or death (infarction) of heart muscle tissue (myocardium).

The term "stroke", as used herein, refers to a rapidly developing loss of brain function(s) due to disturbance in the blood supply to the brain, caused by a blocked or burst blood vessel. This can be due to ischemia (lack of glucose and oxygen supply) caused by thrombosis or embolism or due to a hemorrhage. As a result, the affected area of the brain is unable to function, leading to, for example, inability to move one or more limbs on one side of the body, inability to understand or formulate speech, or inability to see one side of the visual field.

A "neurological disease" or "neurological disorder" as used herein, is a disease or disorder that affects the nervous system of a subject including a disease that affects the brain, spinal cord, or peripheral nerves. A neurological disease or disorder may affect the nerve cells or the supporting ells of the nervous system, such as the glial cells. The causes of neurological disease or disorder include infection, inflammation, ischemia, injury, tumor, or inherited illness.

A disease or disorder is "alleviated" if the severity of a symptom of the disease or disorder, or the frequency with which such a symptom is experienced by a subject, or both, are reduced.

The term "non-degenerative neurological disease," as used herein, refers to a neurological disease or disorder that is not characterized by progressive neuronal death or degeneration, but that is associated with elevated sPLA2 levels or activity detectable in a body sample obtained from a subject.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-CCGTT-3' and 5'-CGGTAT-3' share 75% homology.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, Carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

An "inducible" promoter is a nucleotide sequence which, when operably linked with a polynucleotide which encodes or specifies a gene product, causes the gene product to be produced substantially only when an inducer which corresponds to the promoter is present.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.
The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "recombinant DNA" as used herein is defined as DNA produced by joining pieces of DNA from different sources.

The term "recombinant polypeptide" as used herein is defined as a polypeptide produced by using recombinant DNA methods.

By the term "specifically binds," as used herein, is meant a molecule, such as an antibody, which recognizes and binds to another molecule or feature, but does not substantially recognize or bind other molecules or features in a sample.

A "prophylactic" treatment is a treatment administered to a subject who does not exhibit signs of a disease or exhibits only early signs of the disease for the purpose of decreasing the risk of developing pathology associated with the disease.

"Preventing" a disease, as the term is used herein, means that the onset of the disease is delayed, and/or that the symptoms of the disease will be decreased in intensity and/or frequency, when an inhibitor is administered compared with the onset and/or symptoms in the absence of the inhibitor.

As used herein, the term "alleviate" refers to the lessening, decrease, or diminishing of a symptom, state, or condition. In one aspect, a symptom of a disease is alleviated when the symptom decreases in severity of occurrence or effect in a patient. In another aspect, a symptom of a disease is alleviated when the symptom is completely eradicated or eliminated from the patient.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the term "degeneration of a neuron" refers to any decrease in activity, viability, or function of a neuron from the normal healthy state of the neuron. In one aspect, degeneration of a neuron refers to a minor decrease in activity, viability, or function of a neuron from the normal healthy state of the neuron. In another aspect, degeneration of a neuron refers to the complete incapacitation of the neuron such that the neuron cannot function in any capacity, and even death of the neuron. The term "degeneration of axon" similarly refers to the activity, viability or function of an axon.

The term "treatment," as used herein, refers to reversing, alleviating, delaying the onset of, inhibiting the progress of, and/or preventing a disease or disorder, or one or more symptoms thereof, to which the term is applied in a subject. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

"Substantially similar function" refers to the function of a modified nucleic acid or a modified protein, with reference to the wild-type CHEC-9 or CHEC-7 nucleic acid or wild-type CHEC-9 or CHEC-7 polypeptide. The modified polypeptide will be substantially homologous to the wild-type CHEC-9 or CHEC-7 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type CHEC-9 or CHEC-7 polypeptide. Alternatively, the similarity of function (activity) of the modified polypeptide may be higher than the activity of the wild-type CHEC-9 or CHEC-7 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type CHEC-9 or CHEC-7 nucleic acid encodes the modified protein described above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range. It is understood that any and all whole or partial integers between any ranges set forth herein are included herein.

DESCRIPTION

The present invention comprises compositions and methods of treating a mammal afflicted with or at risk for developing a non-degenerative neurological disease or associated with elevated sPLA2 activity. The method comprises administering to a mammal an effective amount of a sPLA2 inhibitor to a mammal as a prophylactic or therapeutic treatment. The present invention further comprises compositions and methods of treating a mammal afflicted with or at risk for developing cardiovascular disease. Preferably, the mammal is human.

A preferred sPLA2 inhibitor is a CHEC peptide, most preferably a CHEC-9, CHEC-7, or a functionally equivalent variant thereof. CHEC peptides, nucleic acids encoding CHEC peptides, and pharmaceutical preparations comprising the same, have broad utility in the treatment of neurological diseases and disorders where sPLA2 levels of activity are deleteriously elevated in a mammal and/or have an inflammatory component. The uses of these materials in the methods described herein below are intended to exemplify their utility, and are not intended to limit the invention.

I. Compositions

A nine amino acid peptide CHEASAAQC (SEQ ID NO. 1) designated CHEC-9 or CH-QC9 and a CHEC-9 peptide variant having the sequence CAHAQAESC (SEQ ID NO. 2) have been found to inhibit phospholipase A2 (U.S. Pat. No. 7,528,112, U.S. Pat. No. 6,262,024, U.S. patent application Ser. No. 11/974,527; U.S. patent application Ser. No. 11/988,253, and U.S. patent application Ser. No. 12/436, 066). A seven amino acid peptide, CHEC-7 having the sequence CHEASQC (SEQ ID NO. 3), is even more potent as a sPLA2 inhibitor than CHEC-9 (U.S. patent application Ser. No. 11/974,527).

The nucleic acid sequence, TGCCATGAAGCATCA-GCAGCTCAATGC (SEQ ID NO, 4) or TGCCAT-GAAGCATCAGCAGCTCAATGT (SEQ ID NO. 5), encode the CHEC-9 peptide where the last cysteine (C) of SEQ ID NO. 4 is used to cyclize the peptide for certain applications. The nucleic acid sequence, TGCCAT-GAAGCATCACAATGC (SEQ ID NO. 6) or TGCCAT-GAAGCATCACAATGT (SEQ ID NO. 7), encode the CHEC-7 peptide where the last cysteine (C) of SEQ ID NO. 6 is used to cyclize the peptide for certain applications.

A. Preparation of CHEC-Encoding Nucleic Acid Molecules

Nucleic acid molecules encoding CHEC peptides of the invention may be prepared by two general methods: (1) synthesis from appropriate nucleotide triphosphates, or (2) isolation from biological sources. Both methods utilize protocols well known in the art. Preparation of an isolated nucleic acid molecule of the invention may be by oligonucleotide synthesis. The nucleic acid synthesized may be any combination of codons which encode a CHEC peptide. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Alternatively, nucleic acid sequences encoding a CHEC peptide may be isolated from appropriate biological sources using methods known in the art. Suitable probes for this purpose are derived from sequences which encode the amino acids of a CHEC peptide.

The nucleotide sequences encoding a CHEC peptide can comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are variants the nucleotide sequences recited herein that encode a CHEC peptide.

A nucleotide sequence that is a variant or a nucleotide sequence encoding a CHEC peptide can typically be isolated from a recombinant cell or organism by means of introducing conservative or non-conservative substitutions in the nucleic acid sequence that encodes a CHEC peptide. Other examples of possible modifications include the insertion of one or more nucleotides in the sequence, the addition of one or more nucleotides in any of the ends of the sequence, or the deletion of one or more nucleotides in any end or inside the sequence.

In another aspect, the invention relates to a construct, comprising a nucleotide sequence encoding a CHEC peptide. In a particular embodiment, the construct is operatively bound to transcription, and optionally translation, control elements. The construct can incorporate an operatively bound regulatory sequence of the expression of the nucleotide sequence of the invention, thus forming an expression cassette.

In accordance with the present invention, nucleic acids having the appropriate level of sequence homology with a nucleic acid sequence encoding a CHEC peptide of the invention may be identified by using hybridization and washing conditions of appropriate stringency. For example, hybridizations may be performed, according to the method of Sambrook et al., 2001, Molecular Cloning: A Laboratory Manual, Cold Spring Harbor Laboratory Press, Cold Spring Harbor, N.Y., using a hybridization solution comprising: 5×SSC, 5×Denhardt's reagent, 1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% 5 SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_m = 81.5° C. + 16.6 \log [Na^+] + 0.41 (\% G+C) - 0.63 (\% \text{formamide}) - 600/\#bp \text{ in duplex}$$

As an illustration of the above formula, using $[Na^+]=[0.368]$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is 5 defined as hybridization in 6×SSC, 5×Denhardt's solution, 0.5% SDS and 100 mg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's 10 solution, 0.5% SDS and 100 μg/ml denatured salmon sperm DNA at 42° C., and washed in 0.1×SSC and 0.5% SDS at 65° C. for 15 minutes.

CHEC peptide-encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention. As mentioned previously, such oligonucleotides are useful as probes for detecting or isolating related CHEC peptide encoding nucleic acids.

It will be appreciated by persons skilled in the art that variants (e.g., allelic variants) of nucleic acid sequences encoding a CHEC peptide exist in the human population, and must be taken into account when designing and/or utilizing oligonucleotides of the invention. Accordingly, it is within the scope of the present invention to encompass such variants, with respect to the CHEC sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants.

B. Preparation of CHEC Peptides

CHEC-9 peptide, CHEC-7 peptide, and functional variants thereof may be prepared in a variety of ways, according to known methods. The peptide may be synthesized using an automated peptide synthesizer. Alternatively, the peptide may be purified from appropriate sources, e.g., transformed bacterial or animal cultured cells or tissues, by immunoaffinity purification. The availability of nucleic acid molecules encoding CHEC peptides enables production of the peptide using in vitro expression methods known in the art. For example, a CHEC-9 encoding polynucleotide may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or Gibco-BRL, Gaithersburg, Md.

Alternatively, larger quantities of CHEC peptides may be produced by expression in a suitable prokaryotic or eukaryotic system. For example, part or all of a DNA molecule, such as a nucleic acid encoding CHEC-9 may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

A CHEC peptide produced by gene expression in a recombinant prokaryotic or eukaryotic system may be purified according to methods known in the art. In a preferred embodiment, a commercially available expression/secretion system can be used, whereby the recombinant peptide/protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

A CHEC-9 peptide, CHEC-7 peptide, and functional homologs or variants thereof, prepared by the aforementioned methods, may be analyzed according to standard procedures. For example, such proteins may be subjected to amino acid sequence analysis, according to known methods. One such peptide variant which also has neuron protective activity is the peptide having the sequence CAHAQAESC (SEQ ID NO. 2).

A CHEC peptide may be oxidized (cyclized, e.g. as in SEQ ID NO. 4 or SEQ ID NO. 6), or alkylated (linearized) or otherwise post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103, 489) to a standard translation reaction.

A polypeptide of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

A peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The CHEC peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

II. Methods

The present invention provides a method of treating or preventing a non-degenerative neurological disease or disorder associated with an elevated level of sPLA2 activity in a mammal. The method comprises administering to a mammal afflicted with a non-degenerative neurological disease or disorder, or at-risk of developing a non-degenerative neurological disease or disorder, a therapeutically effective amount of at least one sPLA2 inhibitor, wherein the sPLA2 inhibitor inhibits the activity of sPLA2, thereby treating or preventing the non-degenerative neurological disease or disorder. A preferred sPLA2 inhibitor of the invention is a CHEC-9 peptide, a CHEC-7 peptide, or a functionally equivalent variant thereof.

Examples of non-degenerative neurological diseases and disorders associated with elevated sPLA2 activity include, but are not limited to, epilepsy, ischemic injury, schizophrenia, and mood disorders. It will be understood by the skilled artisan that the invention should not be limited to those diseases explicitly recited herein, but that the instant invention has utility in the treatment of any non-degenerative neurological disease or disorder which might benefit from treatment using a phospholipase A2 inhibitor. Methods of prophylaxis (i.e., prevention or decreased risk of disease), as well as reduction in the frequency or severity of symptoms associated with elevated sPLA2 or any related disease or disorder, are also encompassed by the present invention.

In a preferred embodiment, the mammal is a human.

In one embodiment, the present invention provides a method of treating a mammal afflicted with or at risk of developing epilepsy associated with elevated levels of sPLA2. The method comprises administering a therapeutically effective amount of a CHEC peptide, or a pharmaceutical composition comprising a therapeutically effective amount of a CHEC peptide, to a mammal afflicted with epilepsy, wherein the CHEC peptide inhibits sPLA2 activity, thereby treating the epilepsy.

In another embodiment, the present invention provides a method of treating a mammal at risk of having a seizure and where sPLA2 levels are elevated. The method comprises administering a therapeutically effective amount of a CHEC peptide, or a pharmaceutical composition comprising a therapeutically effective amount of a CHEC peptide, to a mammal at risk of having a seizure, wherein the CHEC peptide inhibits sPLA2 activity, thereby preventing a seizure.

In still another embodiment, the present invention provides a method of treating a mammal afflicted with or at risk of developing a non-degenerative neurological disease or disorder associated with an elevated level of sPLA2 where the method comprises administering a therapeutically effective amount of a CHEC peptide, or a pharmaceutical composition comprising a therapeutically effective amount of a CHEC peptide, to a mammal afflicted with a non-degenerative neurological disease or disorder associated with elevated sPLA2 activity, such that when the sPLA2 inhibitor contacts a neuron in the central or peripheral nervous system, the sPLA2 inhibitor inhibits sPLA2 activity in the neuron thereby treating the non-degenerative neurological disease or disorder.

In another embodiment, the present invention provides a method of treating a mammal afflicted with or at risk of developing an ischemic injury to CNS tissue. The method comprises administering a therapeutically effective amount of a CHEC peptide, or a composition comprising a CHEC peptide, to a mammal afflicted with ischemia or a mammal at risk of ischemic injury to CNS tissue, wherein the CHEC peptide inhibits sPLA2 activity, thereby treating or preventing the ischemic injury.

In still another embodiment, the present invention provides a method of treating a mammal afflicted with or at risk of developing schizophrenia. The method comprises administering a therapeutically effective amount of a CHEC peptide, or a composition comprising a therapeutically effective amount of a CHEC peptide, to a mammal afflicted with schizophrenia, wherein the CHEC peptide inhibits sPLA2 activity, thereby treating the schizophrenia.

In still another embodiment, the present invention provides a method of treating a mammal afflicted with or at risk of developing a mood disorder. The method comprises administering a therapeutically effective amount of a CHEC peptide, or a composition comprising a therapeutically effective amount of a CHEC peptide, to a mammal afflicted with a mood disorder, wherein the CHEC peptide inhibits sPLA2 activity, thereby treating the mood disorder.

In another embodiment, the present invention provides a method of treating a mammal afflicted with or at risk of developing a cardiovascular disease or disorder. The method comprises administering a therapeutically effective amount of a CHEC peptide, or a composition comprising a therapeutically effective amount of a CHEC peptide, to a mammal afflicted with a cardiovascular disease or disorder, wherein the CHEC peptide inhibits sPLA2 activity, thereby treating the cardiovascular disease or disorder. In one aspect, a cardiovascular disease or disorder is associated with elevated sPLA2 expression or activity. In another aspect, a cardiovascular disease or disorder is not be associated with elevated sPLA2 expression or activity, but inhibition of sPLA2 expression or activity is still an efficacious treatment of the disease or disorder. Methods of prophylaxis (i.e., prevention or decreased risk of disease), as well as reduction in the frequency or severity of symptoms associated with sPLA2 activity as it relates to a cardiovascular disease or disorder, are also encompassed by the present invention.

In another embodiment, the present invention provides a method of treating a mammal afflicted with or at risk of developing atherosclerosis. The method comprises administering a therapeutically effective amount of a CHEC peptide, or a composition comprising a therapeutically effective amount of a CHEC peptide, to a mammal afflicted with or at risk of developing atherosclerosis, wherein the CHEC peptide inhibits sPLA2 activity, thereby inhibiting, reducing, or preventing plaque formation in a blood vessel and treating atherosclerosis.

In still another embodiment, the present invention provides a method of treating a mammal afflicted with or at risk of developing angina. The method comprises administering a therapeutically effective amount of a CHEC peptide, or a composition comprising a therapeutically effective amount of a CHEC peptide, to a mammal afflicted with or at risk of developing angina, wherein the CHEC peptide inhibits sPLA2 activity, thereby treating angina.

In yet another embodiment, the present invention provides a method of treating a mammal afflicted with or at risk of developing cerebrovascular accident (stroke). The method comprises administering a therapeutically effective amount of a CHEC peptide, or a composition comprising a therapeutically effective amount of a CHEC peptide, to a mammal afflicted with or at risk of developing cerebrovascular accident, wherein the CHEC peptide inhibits sPLA2 activity, thereby treating cerebrovascular accident (stroke).

In another embodiment, the present invention provides a method of treating a mammal afflicted with or at risk of developing cerebrovascular disease. The method comprises administering a therapeutically effective amount of a CHEC peptide, or a composition comprising a therapeutically effective amount of a CHEC peptide, to a mammal afflicted with or at risk of developing cerebrovascular disease, wherein the CHEC peptide inhibits sPLA2 activity, thereby treating cerebrovascular disease.

In yet another embodiment, the present invention provides a method of treating a mammal afflicted with or at risk of developing transient ischemic incidents. The method comprises administering a therapeutically effective amount of a CHEC peptide, or a composition comprising a therapeutically effective amount of a CHEC peptide, to a mammal afflicted with or at risk of developing transient ischemic incidents, wherein the CHEC peptide inhibits sPLA2 activity, thereby treating transient ischemic incidents.

In still another embodiment, the present invention provides a method of treating a mammal afflicted with or at risk of developing congestive heart failure. The method comprises administering a therapeutically effective amount of a CHEC peptide, or a composition comprising a therapeutically effective amount of a CHEC peptide, to a mammal afflicted with or at risk of developing congestive heart failure, wherein the CHEC peptide inhibits sPLA2 activity, thereby treating congestive heart failure.

In another embodiment, the present invention provides a method of treating a mammal afflicted with or at risk of developing coronary artery disease. The method comprises administering a therapeutically effective amount of a CHEC peptide, or a composition comprising a therapeutically effective amount of a CHEC peptide, to a mammal afflicted with or at risk of developing coronary artery disease, wherein the CHEC peptide inhibits sPLA2 activity, thereby treating coronary artery disease.

In yet another embodiment, the present invention provides a method of treating a mammal afflicted with or at risk of developing myocardial ischemia. The method comprises administering a therapeutically effective amount of a CHEC peptide, or a composition comprising a therapeutically effective amount of a CHEC peptide, to a mammal afflicted with or at risk of developing myocardial ischemia, wherein the CHEC peptide inhibits sPLA2 activity, thereby treating myocardial ischemia.

In still another embodiment, the present invention provides a method of treating a mammal afflicted with or at risk of developing myocardial infarction a. The method comprises administering a therapeutically effective amount of a CHEC peptide, or a composition comprising a therapeutically effective amount of a CHEC peptide, to a mammal afflicted with or at risk of developing myocardial infarction, wherein the CHEC peptide inhibits sPLA2 activity, thereby treating myocardial infarction.

In another embodiment, the present invention provides a method of treating a mammal afflicted with or at risk of developing peripheral vascular disease. The method comprises administering a therapeutically effective amount of a CHEC peptide, or a composition comprising a therapeutically effective amount of a CHEC peptide, to a mammal afflicted with or at risk of developing peripheral vascular disease, wherein the CHEC peptide inhibits sPLA2 activity, thereby treating peripheral vascular disease.

Methods of Delivering a CHEC Peptide to a Cell

The present invention comprises a method for treating or preventing a non-degenerative neurological disease or disorder in a mammal where the disease or disorder is at least in part caused by elevated activity of sPLA2. In particular, the present invention comprises a method for treating or preventing epilepsy, ischemic injury of CNS tissues, schizophrenia, and mood disorders. Accordingly, the method comprises administering a therapeutic amount of a sPLA2 inhibitor to a mammal.

The present invention further comprises a method of treating or preventing cardiovascular disease in a mammal. In particular, the present invention comprises a method of treating or preventing atherosclerosis, angina, cerebrovascular accident (stroke), cerebrovascular disease, transient ischemic incidents, congestive heart failure, coronary artery disease, myocardial ischemia, myocardial infarction, and peripheral vascular disease.

Nucleic acid molecules which encode a CHEC peptide, e.g. SEQ ID NO. 4 or SEQ ID NO. 5, may be incorporated in a known manner into an appropriate expression vector which ensures expression of the CHEC peptide.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al., 2001, Molecular Cloning: A Laboratory Manual, Cold Spring Harbor Laboratory Press, Cold Spring Harbor, N.Y. and in Ausubel et al. 2002, Current Protocols in Molecular Biology, John Wiley & Sons, NY, and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2001, Molecular Cloning: A Laboratory Manual, Cold Spring Harbor Laboratory Press, Cold Spring Harbor, N.Y.). In a particular embodiment, the vector is a vector useful for transforming animal cells.

The recombinant expression vectors may also contain nucleic acid molecules which encode a protein which provides increased expression of the recombinant CHEC peptide; increased solubility of the recombinant CHEC peptide; and/or aid in the purification of the recombinant CHEC peptide by acting as a ligand in affinity purification. For example, a proteolytic cleavage site may be inserted in the recombinant peptide to allow separation of the recombinant CHEC peptide after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al., 2001, Molecular Cloning: A Laboratory Manual, Cold Spring Harbor Laboratory Press, Cold Spring Harbor, N.Y. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, neuron specific promoters such as synapsin 1, calcium/calmodulin-dependent protein kinase II, tubulin beta 3, glial fibrillary acidic protein (GFAP), neuron-specific enolase, and platelet-derived growth factor beta chain promoters.

In a particular embodiment, the expression of the nucleic acid is externally controlled. In a more particular embodiment, the expression is externally controlled using the doxycycline Tet-On system.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al., (2001, Molecular Cloning: A Laboratory Manual, Cold Spring Harbor Laboratory Press, Cold Spring Harbor, N.Y.), and other laboratory textbooks. For example, a CHEC peptide may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

III. Pharmaceutical Compositions and Therapies

Administration of a sPLA2 inhibitor comprising one or more CHEC peptides, or a variant or derivative thereof, in a method of treatment can be achieved in a number of different ways, using methods known in the art. Such methods include, but are not limited to, providing an exogenous CHEC peptide inhibitor to a subject or expressing a recombinant CHEC peptide inhibitor expression cassette.

The therapeutic and prophylactic methods of the invention thus encompass the use of pharmaceutical compositions comprising a sPLA2 inhibitor, preferably a CHEC peptide of the invention or an isolated nucleic acid encoding a CHEC peptide of the invention to practice the methods of the invention. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 μM and 10 μM in a mammal.

Typically, dosages which may be administered in a method of the invention to an animal, preferably a human, range in amount from 0.5 μg to about 50 mg per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 μg to about 10 mg per kilogram of body weight of the animal. More preferably, the dosage will vary from about 3 μg to about 1 mg per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, parenteral, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents useful in the treatment of epilepsy as well as other neurological diseases and disorders. By way of a non-limiting example, active agents useful in the treatment of epilepsy are well known in the art. Anticonvulsants compounds include, but are not limited to, carbamazepine (common US brand name Tegretol), clorazepate (Tranxene), clonazepam (Klonopin), ethosuximide (Zarontin), felbamate (Felbatol), fosphenyloin (Cerebyx), gabapentin (Neurontin), lacosamide (Vimpat), lamotrigine (Lamictal), levetiracetam (Keppra), oxcarbazepine (Trileptal), phenobarbital (Lminal), phenyloin (Dilantin), pregabal in (Lyrica), primidone (Mysoline), tiagabine (Gabitril), topiramate (Topamax), valproate semisodium (Depakote), valproic acid (Depakene), and zonisamide (Zonegran), clobazam (Frisium) and vigabatrin (Sabril), retigabine, brivaracetam, and seletracetam, diazepam (Valium, Diastat) and lorazepam (Ativan), paraldehyde (Paral), midazolam (Versed), and pentobarbital (Nembutal), acetazolamide (Diamox), progesterone, adrenocorticotropic hormone (ACTH, Acthar), various corticotropic steroid hormones (prednisone), or bromide. Anxiolytics include, but are not limited to, benzodiazepines, such as Alprazolam, Chlordiazepoxide, Clonazepam, Diazepam, Lorazepam; 5-HT receptor agonists, such as azapirones, barbiturates, hydroxyzine, beta-blockers such as propranolol and oxprenolol.

In another embodiment, in addition to the active ingredient, a pharmaceutical composition of the invention may further comprise one or more additional pharmaceutically active agents useful in the treatment of atherosclerosis as well as other cardiovascular diseases and disorders. By way of a non-limiting example, active agents useful in the treatment of atherosclerosis are well known in the art and include include, but are not limited to, lipid-lowering compounds, such as statins and niacin, which reduce blood levels of fats such as cholesterol and triglycerides, and antithrombotic drugs, including warfarin, low-dose aspirin, and elopidogrel, which prevent further plaque accumulation, mitigate injuries from blood clots caused by atherosclerosis, and treat heart disease.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

IV. Kits

The invention also includes a kit comprising a sPLA2 inhibitor of the invention and an instructional material which describes, for instance, administering the sPLA2 inhibitor to a subject as a prophylactic or therapeutic treatment or a non-treatment use as described elsewhere herein. A preferred sPLA2 inhibitor is a CHEC peptide, including CHEC-9, CHEC-7, or a derivative or variant, thereof. In an embodiment, this kit further comprises a (preferably sterile) pharmaceutically acceptable carrier suitable for dissolving or suspending the therapeutic composition, comprising a sPLA2 inhibitor, or a combination thereof of the invention, for instance, prior to administering the molecule to a subject. Optionally, the kit comprises an applicator for administering the inhibitor.

A kit providing a nucleic acid encoding a peptide or antibody of the invention and an instructional material is also provided.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Synthesis of Peptides

Peptide synthesis was performed at the Protein Chemistry Laboratory in the Department of Pathology and Laboratory Medicine University of Pennsylvania as well as by Celtek Bioscience (Nashville, Tenn.). The peptides were HPLC purified on a C18 column, dried, reconstituted in water and dried again. Peptide stock solutions (200-250 µg/ml, 218-273 µM) were prepared in 50 mM tris pH=7.4 or DMEM and incubated at room temperature overnight or for 2 hrs at 37°. Free sulphydryls were measured using Ellman's reagent (DTNB, 0.04 mg/ml) in 0.1M $NaH_2PO_4$, 20 mM EDTA, pH=8 by mixing 25 µl sample with 275 µl reaction buffer. Absorbance of these samples was measured at 450 nm with a 808-x1 microplate reader (Biotek Instruments), and was at background levels after cross-linking. In addition, the formation of intramolecular disulphide bond in selected samples was verified by determining the exact molecular mass of the unfolded versus folded peptides using electrospray mass spectrometry (LC-ZQ Mass Spectrometer, Waters).

Kainic Acid Seizure Model

Kainic acid (KA) was administered intraperitoneal (IP) to rats at doses ranging from 5-10 mg/kg. Rats age postnatal day (P) 12-15 were administered 2 mg/kg KA. Rats age P35-40 were administered 6 mg/kg KA. The KA was delivered in a constant volume of phosphate buffer (5 ml/kg) and reliably produced motor seizure activity.

Following IP administration of KA, rats were videorecorded for 3 hours, and then daily for 3 hours. The video recordings are later scored blind. The severity and latency of seizures is graded for P35 rats by a classical scale shown in Table 1 (Racine, 1972, Electroencephalog. Clin. Neurophysiol. 32:281-294).

For younger rats (P12-15), the less severe motor seizure stages consist of scratching-like movements of the hind paws and "wet dog shakes." Increased seizure severity in P12-15 rats includes clonic (and sometimes tonico-clonic) seizures involving movements of all four paws and associated with head tremor. While severe, these seizures do not usually evolve into status epilepticus.

TABLE 1

Scale fro grading seizures in rats aged P35-40.

| Stage | Characteristic motor activity |
|---|---|
| 1 | hypoactivity, mouth and facial automatism |
| 2 | head nodding and mastication |
| 3 | forelimb clonus without rearing |
| 4 | bilateral forelimb clonus and rearing |
| 5 | rearing and loss of posture |
| Status epilepticus | stage 4-5 lasting for 30 min, |

Rats (250-300 g) are done in pairs and administered either a control peptide/vehicle or CHEC peptide in vehicle at various intervals pre- or post KA treatment. The route of administration is either oral or subcutaneous, as indicated in the figure legends. Control or CHEC peptide are administered either 4, 2 or 0.5 hours pre-KA or 0.25, and 0.5 hrs post-KA. The effects of CHEC-7 and CHEC-9 are compared because the peptides have different pharmakinetic profiles in rat.

Histology

Following behavioral studies, all rats are deeply anesthetized and perfused transcardially with 4% paraformaldehyde in 0.1M phosphate buffer. Brains are removed and sectioned serially at 20 μm on a cryostat and stained using standard histological techniques. Brain tissue sections are stained with cresyl violet to analyze brain tissue integrity, or stained for the cell specific markers for macrophages/microglia (ED-1) neuronal tubulin (TUJ1), neuronal nuclei (neuN) or neurofilament (NFm) to demonstrate the accumulation of macrophages and microglia.

The results of the experiments presented in this Example are now described.

Experimental Example 1

Effect of CHEC-9 on KA Induced Motor Seizures in Rats

Male (M; n=8) and female (F; n=6) rats (250-300 g) were administered KA at the dosages shown in Table 2. Forty minutes prior to KA administration, the rats were administered either control peptide or CHEC-9 at the indicated dosages and routes of administration. The resulting motor seizures were graded as described elsewhere herein. Rats that were given vehicle control were more likely to exhibit severe motor seizures than rats that were administered CHEC-9. In one set of experiments, rats were pre-fed lecithin or phosphatidylcholine prior to administering the KA.

TABLE 2

| Rat no. | Gender | C9 Dose mg/kg-route | KA mg/kg ip | Max Seizure Stage** |
|---|---|---|---|---|
| K | F | V | 5 | Stat Ep |
| L | F | 0.5-sc | 5 | 1 |
| M | M | 0.5-sc | 5 | 1 |
| N | M | V | 5 | Stat Ep |
| O | M | V | 6 | Died |
| P | M | 0.5-sc | 6 | 2 |
| S | M | 1.0 po | 5 | 1 |
| T | M | V | 5 | 1 |
| U | M | 1.0 po | 10 | 1 |
| V | M | V | 10 | Stat Ep |
| W | F | 1.0 po | 10 | 3 |
| X | F | V | 10 | Stat Ep |
| Y | F | V | 10 | 4 |

Experimental Example 2

Effect of CHEC-9 on Multiunit Activity in Hippocampus in Kainic Acid Treated Rats Rats were implanted with a multichannel electrode bundle placed in the CA1 cell field of the hippocampus one week prior to the experiment. Baseline hippocampal neuronal activity (impulses per second) was collected during a 30 minute control period. After 30 minutes of baseline neuronal activity was collected, either CHEC-9 (1 mg/kg) or vehicle was administered orally 40 min prior to IP administration of kainic acid (10 mg/kg). The duration of the KA administration varied. Neuronal activity in response to KA administration is presented as % of baseline activity (FIG. 1). KA reliably enhanced neuronal activity in a dose-dependent manner in animals that were treated with vehicle. Animals that were treated with CHEC-9 exhibit a much smaller effect of KA on neuronal activity. The vehicle treated rat reached status epilepticus by the end of the experiment, while the peptide treated rat showed no obvious symptoms.

Experimental Example 3

Plasma and Urinary sPLA2 Activity Following Seizure in Humans

Serum or urinary sPLA2 levels are expected to be elevated following seizure activity for a limited time. In order to identify this clinical window when patients are vulnerable to secondary seizure, two patient groups of 25 patients each are assessed for sPLA2 activity in urine and serum. Group 1 comprises "acute patients" patients who had a seizure less than 7 days prior to measurements. Group 2 comprises "stable patients" who had a seizure more than 7 days prior to measurements.

All subjects are screened for and excluded based on the presence of inflammatory disorders or potential inflammatory disorders, unrelated to their epilepsy. These include asthma, heart disease, peripheral autoimmune disorders, infections, or any other disorder suspected to have a significant inflammatory component (e.g. diabetes, cystic fibrosis, persistent chronic allergies). Patients that are obese (defined as BMI>95th centile of the 1990 reference data for age and sex) are excluded as are those that have been treated with steroidal or non-steroidal anti-inflammatory drugs in the 24 hours prior to assessment or who have exercised vigorously in the 18 hours prior to assessment, e.g. sporting events, distance runs. In previous studies, these screening procedures resulted in a relatively stable baseline for sPLA2 activity in control subjects.

Patients are also excluded with seizure disorders that have inflammatory or potential inflammatory etiologies since the inflammation accompanying the seizure would not be easily differentiated from that due to the underlying disorder. For example, patients who have febrile seizures or Rasmussen's encephalitis are excluded, as well as patients whose seizures are associated with diseases that have a strong inflammatory component. Patients that have seizures that may be due to CNS tumors are not included.

During this study, a significant percentage (>50%) of samples are collected from patients that represent the extremes of acute and stable populations, i.e. less than 48 hours and greater than 6 months since last seizure. This bias maximizes the difference in enzyme activity and levels of endogenous mediators.

Figure 2:
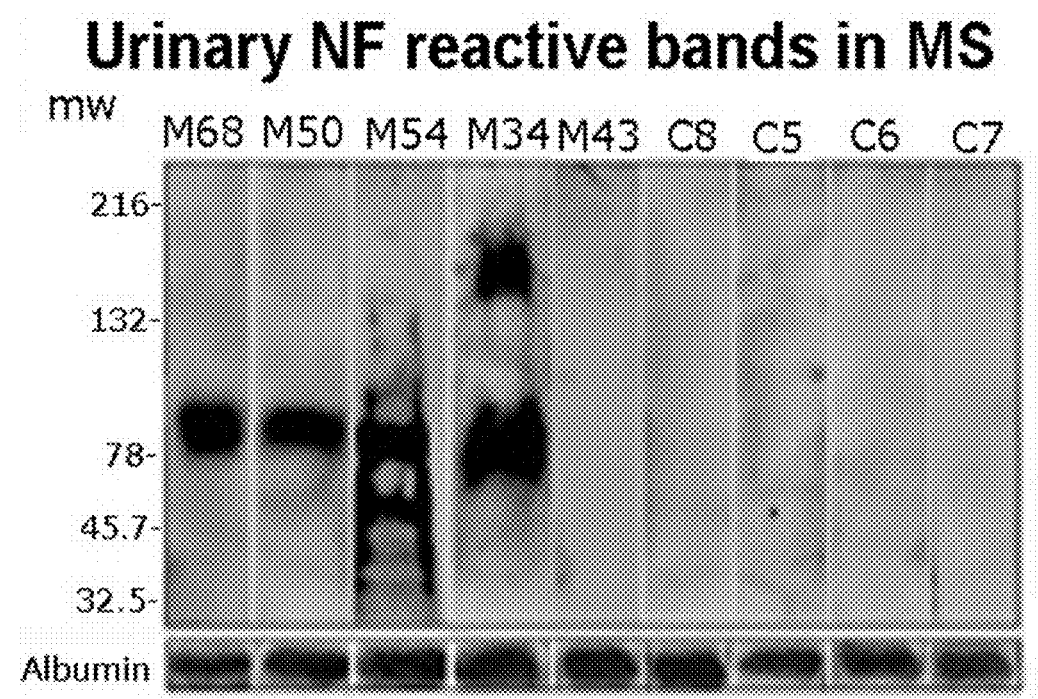
FIG. 2 is an image of a gel depicting the results of a Western blot analysis performed on urine samples obtained from patients diagnosed with multiple sclerosis and probed for the presence of neurofilament (NF) med (160 kDa). Patients with active multiple sclerosis are designated (M) and healthy controls are designated (C). The main band observed is consistent with an 82 kDa calpain fragment of NF med.

Excreted fragments of neuron/CNS-specific proteins, including neurofilament protein (NF med), are measured either by ELISA or Western blotting in urine or serum samples collected from both acute and stable patients. It was found that NF med could be detected in the urine of a significant percentage of patients with multiple sclerosis compared with healthy controls, suggesting NF med is a biomarker for neural damage (FIG. 2). Sections were also immunostained for phosphorylated neurofilament (Sm-32, another marker for neuronal injury), myelin basic protein (MBP), and proteolipid protein (PLP). MBP and PLP identify CNS myelin epitopes and MBP and glycoprotein Po for PNS myelin. These antibodies can be applied to either urine or serum but the blots of the latter are contaminated with large excesses of serum proteins such as albumin or immunoglobulins, making the interpretation of the blots or ELISA assays more difficult. Urine is straightforward after specific proteolytic fragments of these proteins have been identified and confirmed. Changes in levels of neuronal markers, specifically those appearing under conditions of elevated sPLA2 activity after seizures, are measured to obtain an estimate of neuronal degeneration accompanying a seizure.

Urine samples are prepared and stored at −80° C. until analyzed. Samples are coded at the hospital and securely stored with all relevant clinical details. These coded samples are analyzed for sPLA2 activity, lipid mediators, and dialyzed for whole band analysis of Western blots of specific protein fragments as described above. All analyses are conducted blind without patient identifiers or any knowledge of clinical history.

Measurements of sPLA2 activity in plasma and urine in the acute patient group are compared to measurements made for the stable patient group using a non-parametric statistical test (Mann Whitney U). Variables such as seizure frequency, age, elapsed time since last seizure, and seizure medication present at the time of the seizure are tested for association with sPLA2 activity using a statistical test such as Spearman rank correlations.

The principal goal in the development of anti-epilepsy drugs (AEDs) has been to control hyperexcitability. It is only during the last few years that the inflammatory component of the disease has been recognized, a fact that has not significantly impacted pharmacotherapy or drug development. Interestingly, ACTH and corticosteroids have traditionally been considered an alternative therapy for epilepsy, especially for intractable childhood seizures. Their mechanism of action is unknown. In the proposed study, the subjects are likely to be treated with one or more of the currently available anti-seizure medications, so possible effects on the inflammatory response and cell death must be considered. Some AEDs may exaggerate these responses, other are inhibitory. In still other cases, anti-inflammatory effects are suspected but have not been proved (e.g., compounds providing a non-opiate analgesia are more likely to have an anti-inflammatory action). It is recognized that attenuating elevated electrical activity is likely to have neuroprotective effects, especially in the long term. Unfortunately, the data concerning the systemic cytokine response to AEDs in humans is diverse and often contradictory. Since medications can be a significant variable, a list of all medications that a patient is being administered is also compiled. sPLA2 activity is then compared between a patient group identified as taking a particular medication and a patient group identified as not taking that particular medication using a Mann-Whitney U statistical test.

Parameters significantly associated with sPLA2 ($P \leq 0.10$), are verified for independent predictive value of the initial classification (acute versus stable patient) with a multivariate statistical procedure, namely multiple linear regression.

These data provide the general timing of systemic sPLA2 activity changes in relation to the time elapsed since the latest seizure. In an additional study, the period for systemic inflammatory response to seizures is determined by following acute patients longitudinally. The period of sPLA2 elevation (relative to stable patients) represents the period of maximum vulnerability to seizure-induce inflammatory destruction of CNS tissue, presumably instigated by inflammatory mediators and cellular participants in the immune response. Blots of neuronal protein fragments in urine and serum obtained from patients suggest this neuronal vulnerability.

Longitudinal data from patients is collected to determine the length of time patients show elevated activity of inflammatory mediators relative to the frequency and duration of their seizures. For example, urinary sPLA2 activity (pM/min/mg total protein) is compared to seizure magnitude= (estimated number of seizures)×(average seizure duration). These data identify a clinical window during which the CNS is vulnerable to subsequent seizure as well as damage from inflammatory processes that results from seizure. During this time, the administration of CHEC peptides or nucleic acids encoding CHEC peptides can prevent subsequent seizure or CNS damage.

Experimental Example 4

CHEC Peptide Inhibits Atherosclerotic Plaques in JCR:-cp rat

Figure 3:
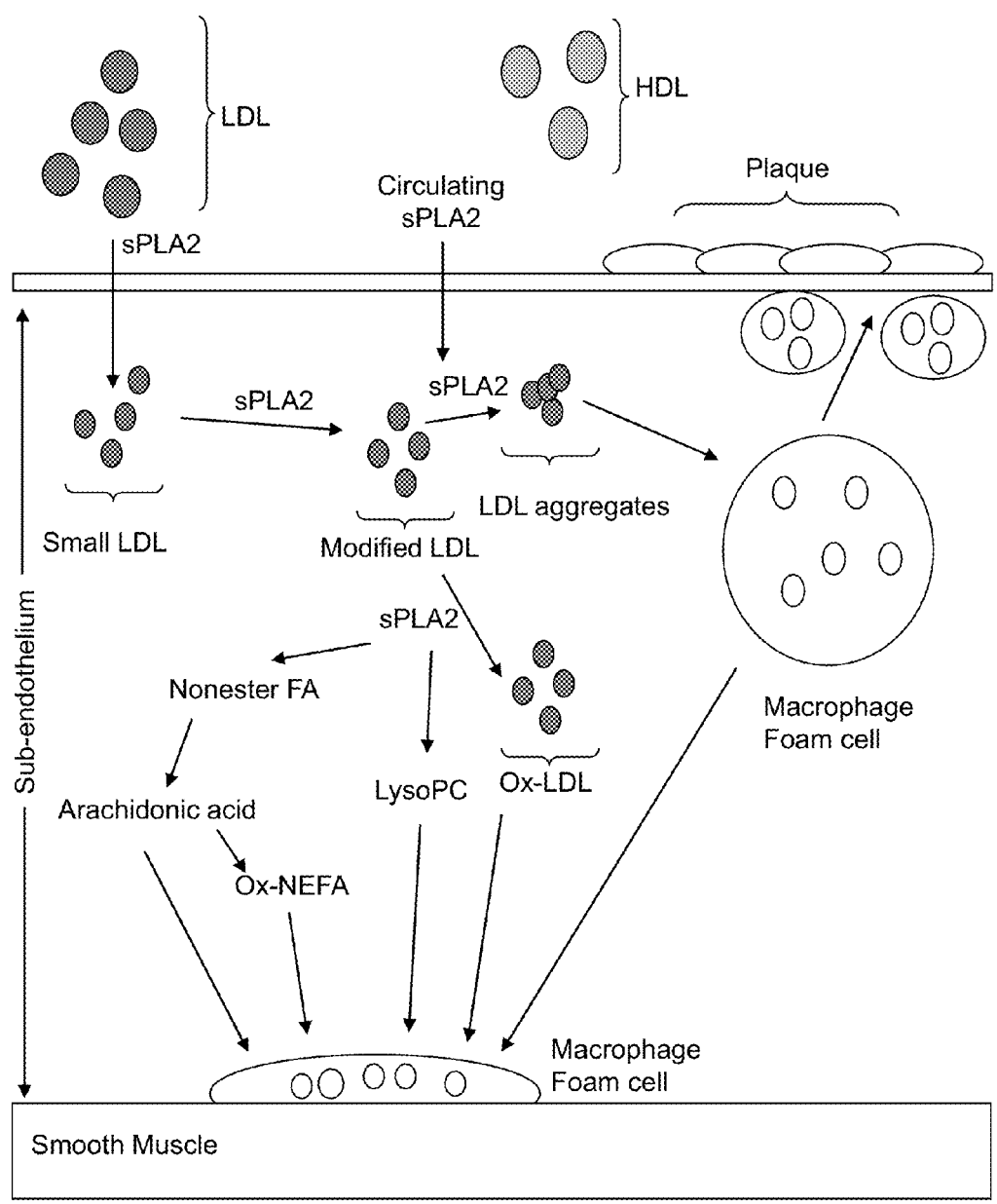
FIG. 3 is a schematic diagram illustrating the various roles sPLA2 plays in atherosclerosis.

As shown in FIG. 3, sPLA2 is an important component at several stages of the biochemical cascade that leads to plaque formation on vessel walls. To begin with, sPLA2s modify lipoprotein particles to prolong their residence time in the circulation and increase penetration into the sub endothelial space (Karabina et al., 2006, FASEB J. 20:2547-2549; Sartipy et al., 1999, J. Biol. Chem. 274:25913-25920; Wooten-Kee et al., 2004, Arterioscler. Thromb. Vasc. Biol. 24:762-767). The remodeling of LDL in the vessel intimae leads to aggregate formation, attack of the aggregates by macrophages, and foam cell formation, the latter facilitated by sPLA2-enhanced cholesterol loading of the cells. The macrophage response and subsequent inflammatory cascade are also sPLA2 dependent, and this continuing process exacerbates the lesion further by increasing plaque size and stimulating collagen deposition (Wooten-Kee et al., 2004, Arterioscler. Thromb. Vasc. Biol. 24; 762-767; Ivandic et al., 1999, Arterioscler. Thromb. Vase. Biol. 19:1284-1290; Ghesquiere et al., 2005, J. Lipid Res. 46:201-210). The CHEC peptides are active in several in vivo models rats and humans (ex vivo) but were less active in mice, which, unlike rats and humans, do not have the gene for the parent polypeptide. Therefore, a suitable and highly reliable rat metabolic model was chosen to test CHEC efficacy for reducing atherosclerotic lesions and myocardial infarction.

The JCR:LA-cp rat is one of a number of strains incorporating the autosomal recessive cp gene. Homozygous cp (cp/cp) rats are obese from an early age, are insulin resistant, and are hyperinsulinemic. They exhibit a marked hyperlipidemia due to hepatic hypersecretion of VLDL. Males also exhibit spontaneous atherosclerosis and ischemic myocardial lesions. Anti-atherosclerotic treatments have been successfully tested in this model (e.g. see O'Brien et al., 2000, Clin Invest Med. 23:124-31; Russell et al., 1998, J. Cardiovasc. Pharmacol. 31:971-977; Russell et al., 1995, Arterioscler Thromb Vase Biol. 15:918-23).

The incidence of atherosclerotic lesions on the aortic arch and of ischemic myocardial lesions in treated and control rats is scored by expert pathological services. The influence of sPLA2 inhibition on specific metabolic parameters such as hyperlipemdemia is tested. These measurements are made starting at 12 weeks and extend to 39 weeks of age. The treatment paradigms comprise daily dosing with CHEC peptides by mouth or gavage for several weeks. During this period, systemic sPLA2 levels and the effects of CHEC peptides on these levels are monitored. In addition, relevant clinical parameters are also monitored such as weight, insulin resistance, insulin levels, and circulating lipid levels. CHEC peptides are administered during overnight watering, as described.

A significant reduction in atherosclerosis related pathologies obtained in an experimentally blinded pathological and blood chemistry analysis suggests that the CHEC peptides are effective therapeutic agents for the treatment of heart disease, vascular disease, and stroke.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a mammal afflicted with epilepsy associated with elevated levels of secreted phospholipase A2 (sPLA2) activity, said method comprising administering a pharmaceutical composition comprising an effective amount of a sPLA2 inhibitor to said mammal, wherein said sPLA2 inhibitor comprises at least one selected from the group consisting of a CHEC-9 peptide and a CHEC-7 peptide, thereby treating said epilepsy in said mammal.

2. The method of claim 1, wherein said mammal is a human.

3. A method of treating a mammal with a seizure disorder associated with elevated secreted phospholipase A2 (sPLA2) activity, said method comprising administering a pharmaceutical composition comprising an effective amount of a sPLA2 inhibitor selected from the group consisting of a CHEC-9 peptide and a CHEC-7 peptide to said mammal, wherein said effective amount of said sPLA2 inhibitor contacts a neuron in the central nervous system, said sPLA2 inhibitor specifically inhibits said sPLA2 activity in said neuron, wherein said sPLA2 inhibitor treats said seizure disorder in said mammal.

4. The method of claim 3, wherein said mammal is a human.

5. A method of treating a mammal afflicted with epilepsy associated with an elevated level of secreted phospholipase A2 (sPLA2) activity in a central nervous system neuron, said method comprising administering a pharmaceutical composition comprising an effective amount of a sPLA2 inhibitor selected from the group consisting of a CHEC-9 peptide and a CHEC-7 peptide to said mammal, wherein when said sPLA2 inhibitor contacts said neuron, said sPLA2 inhibitor specifically inhibits said sPLA2 activity in said neuron, thereby treating said epilepsy in said mammal.

6. The method of claim 5, wherein said mammal is a human.

7. A method of treating a mammal with a seizure disorder associated with elevated secreted phospholipase A2 (sPLA2) activity in a central nervous system neuron, said method comprising administering a pharmaceutical composition comprising an effective amount of a sPLA2 inhibitor selected from the group consisting of a CHEC-9 peptide and a CHEC-7 peptide to said mammal, wherein when said sPLA2 inhibitor contacts said neuron, said sPLA2 inhibitor specifically inhibits said sPLA2 activity in said neuron, thereby treating said seizure disorder in said mammal.

8. The method of claim 7, wherein said mammal is a human.

* * * * *